United States Patent
Belitz et al.

(10) Patent No.: US 10,689,696 B2
(45) Date of Patent: Jun. 23, 2020

(54) METHODS AND SYSTEMS FOR ANALYZING IMAGE DATA

(71) Applicant: Illumina, Inc., San Diego, CA (US)

(72) Inventors: Paul Belitz, San Diego, CA (US); Stephen Tanner, San Diego, CA (US); John S. Vieceli, San Diego, CA (US); Xiaoyu Chen, San Diego, CA (US)

(73) Assignee: ILLUMINA, INC., San Diego, CA (US)

(*) Notice: Subject to any disclaimer, the term of this patent is extended or adjusted under 35 U.S.C. 154(b) by 701 days.

(21) Appl. No.: 15/153,953

(22) PCT Filed: Dec. 3, 2014

(86) PCT No.: PCT/US2014/068409
§ 371 (c)(1),
(2) Date: May 13, 2016

(87) PCT Pub. No.: WO2015/084985
PCT Pub. Date: Jun. 11, 2015

(65) Prior Publication Data
US 2018/0274023 A1    Sep. 27, 2018

Related U.S. Application Data

(60) Provisional application No. 61/911,319, filed on Dec. 3, 2013, provisional application No. 61/915,455, filed on Dec. 12, 2013, provisional application No. 61/915,426, filed on Dec. 12, 2013.

(51) Int. Cl.
*C12Q 1/6869* (2018.01)
*G16B 30/00* (2019.01)

(52) U.S. Cl.
CPC .......... *C12Q 1/6869* (2013.01); *G16B 30/00* (2019.02)

(58) Field of Classification Search
None
See application file for complete search history.

(56) References Cited

U.S. PATENT DOCUMENTS

| 5,916,747 A | 6/1999 | Gilchrist et al. |
| 2010/0034444 A1 | 2/2010 | Emhoff et al. |
| 2012/0020537 A1 | 1/2012 | Garcia et al. |
| 2013/0060482 A1 | 3/2013 | Sikora et al. |
| 2013/0079232 A1 | 3/2013 | Kain et al. |
| 2014/0342921 A1 | 11/2014 | Weiner |

OTHER PUBLICATIONS

"Low-Diversity Sequencing on the Illumina MiSeq Platform", Technical Support Note: Sequencing, May 7, 2013, 1-3.
Golan, D. et al., "Using state machines to model the Ion Torrent sequencing process and to improve read error rates", Bioinformatics, vol. 29 ISMB/ECCB, Jun. 21, 2013, i344-i351.
Kircher, M. et al., "Improved base calling for the Illumina Fenome Analyzer using machine learning strategies", Genome Biology 2009, vol. 10, No. 8, Aug. 14, 2009, R83.
International Preliminary Report on Patentability for PCT.US2014.068409 dated Dec. 11, 2015.
Letter with Demand for PCT.US2014.068409—Oct. 12, 2015.
Search Report and Written Opinion for PCT.US2014.068409—dated Jun. 2, 2015.
John Eid, et al "Real Time DNA Sequencing from Single Polmerase Molecules", Science 323, p. 133-138, (2009).
Nava Whiteford, et al, "Swift: primary data analysis for the Illumina Solexa sequencing platform", Bioinformatics, vol. 25 No. 17 2009, pp. 2194-2199.

*Primary Examiner* — Joseph Woitach
(74) *Attorney, Agent, or Firm* — The Small Patent Law Group LLC; Jason P. Gross

(57) ABSTRACT

Methods and systems for analysis of image data generated from various reference points. Particularly, the methods and systems provided are useful for real time analysis of image and sequence data generated during DNA sequencing methodologies.

23 Claims, 6 Drawing Sheets

METHODS AND SYSTEMS FOR ANALYZING IMAGE DATA

CROSS-REFERENCE TO RELATED APPLICATIONS

The present application claims priority to and the benefit of U.S. Provisional Application Nos. 61/911,319, filed on Dec. 3, 2013; 61/915,455, filed on Dec. 12, 2013; and 61/915,426, filed on Dec. 12, 2013, each of which is incorporated herein by reference in its entirety.

BACKGROUND

The analysis of image data presents a number of challenges, especially with respect to comparing images of an item or structure that are captured from different points of reference. One field that exemplifies many of these challenges is that of nucleic acid sequence analysis.

The detection of specific nucleic acid sequences present in a biological sample has a wide variety of applications, such as identifying and classifying microorganisms, diagnosing infectious diseases, detecting and characterizing genetic abnormalities, identifying genetic changes associated with cancer, studying genetic susceptibility to disease, and measuring response to various types of treatment. A valuable technique for detecting specific nucleic acid sequences in a biological sample is nucleic acid sequencing. Nucleic acid sequencing methodology has evolved significantly from the chemical degradation methods used by Maxam and Gilbert and the strand elongation methods used by Sanger. Today, there are a number of different processes being employed to elucidate nucleic acid sequence. A particularly popular sequencing process is sequencing-by-synthesis. One reason for its popularity is that this technique can be easily applied to massively parallel sequencing projects. For example, using an automated platform, it is possible to carry out hundreds of thousands of sequencing reactions simultaneously. Sequencing-by-synthesis differs from the classic dideoxy sequencing approach in that, instead of generating a large number of sequences and then characterizing them at a later step, real time monitoring of the incorporation of each base into a growing chain is employed. Although this approach might be viewed as slow in the context of an individual sequencing reaction, it can be used for generating large amounts of sequence information in each sequencing cycle when hundreds of thousands to millions of reactions are performed in parallel. Despite these advantages, the vast size and quantity of sequence information obtained through such methods can limit the speed and quality of analysis of sequence data. Thus, there is a need for methods and systems which improve the speed and accuracy of analysis of nucleic acid sequencing data.

BRIEF SUMMARY

Provided herein are methods for evaluating the quality of a base call from a sequencing read. In some embodiments, the methods can comprise the steps of: calculating a set of predictor values for the base call; and then using the predictor values to look up a quality score in a quality table. In some embodiments, the sequencing read utilizes two-channel base calling. In some embodiments, the sequencing read utilizes one-channel base calling. In certain aspects, the quality table is generated using Phred scoring on a calibration data set, the calibration set being representative of run and sequence variability. In certain aspects, the predictor values are selected from the group consisting of: online overlap; purity; phasing; start5; hexamer score; motif accumulation; endiness; approximate homopolymer; intensity decay; penultimate chastity; and signal overlap with background (SOWB). In certain aspects, the set of predictor values comprises online overlap; purity; phasing; and start5. In certain aspects, the set of predictor values comprises hexamer score; and motif accumulation.

In certain aspects, the method further comprises the steps of: discounting unreliable quality scores at the end of each read; identifying reads where the second worst chastity in the first 25 base calls is below a pre-established threshold; and marking the reads as poor quality data. In certain aspects, the method further comprises using an algorithm to identify a threshold of reliability. In certain aspects, reliable base calls comprise q-values, or other values indicative of data quality or statistical significance, above the threshold and unreliable base calls comprise q-values, or other values indicative of data quality or statistical significance, below the threshold. In certain aspects, the algorithm comprises an End Anchored Maximal Scoring Segments (EAMSS) algorithm. In certain aspects, the algorithm uses a Hidden Markov Model that identifies shifts in the local distributions of quality scores.

Also provided herein is a system for evaluating the quality of a base call from a sequencing read, the system comprising: a processor; a storage capacity; and a program for evaluating the quality of a base call from a sequencing read, the program comprising instructions for: calculating a set of predictor values for the base call; and then using the predictor values to look up a quality score in a quality table. In certain aspects, the quality table is generated using Phred scoring on a calibration data set, the calibration set being representative of run and sequence variability. In certain aspects, the predictor values are selected from the group consisting of: online overlap; purity; phasing; start5; hexamer score; motif accumulation; endiness; approximate homopolymer; intensity decay; penultimate chastity; and signal overlap with background (SOWB). In certain aspects, the set of predictor values comprises online overlap; purity; phasing; and start5. In certain aspects, the set of predictor values comprises hexamer score; and motif accumulation.

In certain aspects, the system can further comprise instructions for: discounting unreliable quality scores at the end of each read; identifying reads where the second worst chastity in the first 25 base calls is below a pre-established threshold; and marking the reads as poor quality data. In certain aspects, the system further comprises instructions for using an algorithm to identify a threshold of reliability. In certain aspects, the reliable base calls comprise q-values, or other values indicative of data quality or statistical significance, above the threshold and unreliable base calls comprise q-values, or other values indicative of data quality or statistical significance, below the threshold. In certain aspects, the algorithm comprises an End Anchored Maximal Scoring Segments (EAMSS) algorithm. In certain aspects, the algorithm uses a Hidden Markov Model that identifies shifts in the local distributions of quality scores.

Also presented herein are methods and system for generating a phasing-corrected intensity value. The methods can comprise: performing a plurality of cycles of a sequencing by synthesis reaction such that, at each cycle, a signal is generated indicative of incorporation of the same nucleotide into a plurality of identical polynucleotides, whereby a portion of the signal is noise associated with a nucleotide incorporated during a previous cycle; detecting the signal at each cycle, the signal having an intensity value; and correcting the intensity value for phasing by applying a first order phasing correction to the intensity value; wherein a new first order phasing correction is calculated for each cycle.

In some aspects, the first order phasing correction comprises subtracting an intensity value from the immediately previous cycle from the intensity value of the current cycle. The method can further comprise subtracting an intensity value from the immediately subsequent cycle from the intensity value of the current cycle. In some aspects, the phasing correction comprises: $I_{(cycle)corrected} = I_{(cycle)} {}_N - X^* I_{(cycle)\ N-1} - Y^* I_{(cycle)\ N+1}$. In certain aspects, the values of X and/or Y are chosen to optimize a chastity determination. In certain aspects, the chastity determination comprises mean chastity. In certain aspects, the sequencing run can utilize one-channel, two-channel or four-channel base calling.

Also presented herein are systems for generating a phasing-corrected intensity value. The systems can comprise: a processor; a storage capacity; and a program for generating a phasing-corrected intensity value, the program comprising instructions for: performing a plurality of cycles of a sequencing by synthesis reaction such that, at each cycle, a signal is generated indicative of incorporation of the same nucleotide into a plurality of identical polynucleotides, whereby a portion of the signal is noise associated with a nucleotide incorporated during a previous cycle; detecting the signal at each cycle, the signal having an intensity value; and correcting the intensity value for phasing by applying a first order phasing correction to the intensity value; wherein a new first order phasing correction is calculated for each cycle.

In some aspects, the first order phasing correction comprises subtracting an intensity value from the immediately previous cycle from the intensity value of the current cycle. The method can further comprise subtracting an intensity value from the immediately subsequent cycle from the intensity value of the current cycle. In some aspects, the phasing correction comprises: $I_{(cycle)corrected} = I_{(cycle)} {}_N - X^* I_{(cycle)\ N-1} - Y^* I_{(cycle)\ N+1}$. In certain aspects, the values of X and/or Y are chosen to optimize a chastity determination. In certain aspects, the chastity determination comprises mean chastity. In certain aspects, the sequencing run can utilize one-channel, two-channel or four-channel base calling.

Also presented herein are methods and systems for identifying a nucleotide base from sequencing data where two separate images are obtained of an array of features on a surface. In some embodiments, the method comprises: detecting the presence or absence of a signal in two different channels for each of a plurality of features on an array at a particular time, thereby generating a first set of intensity values and a second set of intensity values for each of the features, wherein the combination of intensity values in each of the two channels corresponds to one of four different nucleotide bases; fitting four Gaussian distributions to the intensity values, each distribution having a centroid; calculating a likelihood value that indicates the likelihood of a particular feature belonging to each of the four distributions; and selecting for each feature of said plurality of features the distribution having the highest likelihood value, wherein said distribution corresponds to the identity of the nucleotide base present at said particular feature.

Also presented herein is a system for evaluating the quality of a base call from a sequencing read, the system comprising: a processor; a storage capacity; and a program for identifying a nucleotide base, the program comprising instructions for: detecting the presence or absence of a signal in two different channels for each of a plurality of features on an array at a particular time, thereby generating a first set of intensity values and a second set of intensity values for each of the features, wherein the combination of intensity values in each of the two channels corresponds to one of four different nucleotide bases; fitting four Gaussian distributions to the intensity values, each distribution having a centroid; calculating a likelihood value that indicates the likelihood of a particular feature belonging to each of the four distributions; and selecting for each feature of said plurality of features the distribution having the highest likelihood value, wherein said distribution corresponds to the identity of the nucleotide base present at said particular feature.

Also presented herein is a method of identifying a nucleotide base, the method comprising: obtaining a first set of intensity values and a second set of intensity values for each a plurality of features on an array, wherein the intensity value for each feature in one or both sets corresponds to the presence or absence of a particular nucleotide base out of four possible nucleotide bases at the feature; fitting four Gaussian distributions to the intensity values, each distribution having a centroid; calculating four likelihood values for each feature, wherein each likelihood value indicates the likelihood of a particular feature belonging to one of the four distributions; and selecting for each feature of said plurality of features the distribution having the highest of the four likelihood values, wherein the distribution corresponds to the identity of the nucleotide base present at the particular feature.

Also presented herein is a system for evaluating the quality of a base call from a sequencing read, the system comprising: a processor; a storage capacity; and a program for identifying a nucleotide base, the program comprising instructions for: obtaining a first set of intensity values and a second set of intensity values for each a plurality of features on an array, wherein the intensity value for each feature in one or both sets corresponds to the presence or absence of a particular nucleotide base out of four possible nucleotide bases at the feature; fitting four Gaussian distributions to the intensity values, each distribution having a centroid; calculating four likelihood values for each feature, wherein each likelihood value indicates the likelihood of a particular feature belonging to one of the four distributions; and selecting for each feature of said plurality of features the distribution having the highest of the four likelihood values, wherein the distribution corresponds to the identity of the nucleotide base present at the particular feature.

In any of the methods and systems described above, certain aspects can include embodiments wherein fitting can comprise using one or more algorithms from the group consisting of: a k-means clustering algorithm, a k-means-like clustering algorithm, expectation maximization, and a histogram based method. In some aspects, fitting can comprise using an Expectation Maximization algorithm. In some aspects, the method can comprise normalizing the intensity values. In certain aspects, a chastity value is calculated for each feature. In certain aspects, the chastity value is a function of the relative distance from a feature to the two nearest Gaussian centroids. In some aspects, features having a chastity value below a threshold value are filtered out.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1A is a scatter plot showing raw intensities for a particular tile and a particular cycle, where the C nucleotide is represented by signal in channel 1 only, A nucleotide is represented by signal in channel 2 only, T nucleotide is represented by signal in both channels 1 and 2, and G nucleotide is "dark. " FIG. 1B shows phasing corrected intensities of the same data using a phasing correction according to one embodiment of the methods presented herein.

DETAILED DESCRIPTION

Figures 1A, 1B:
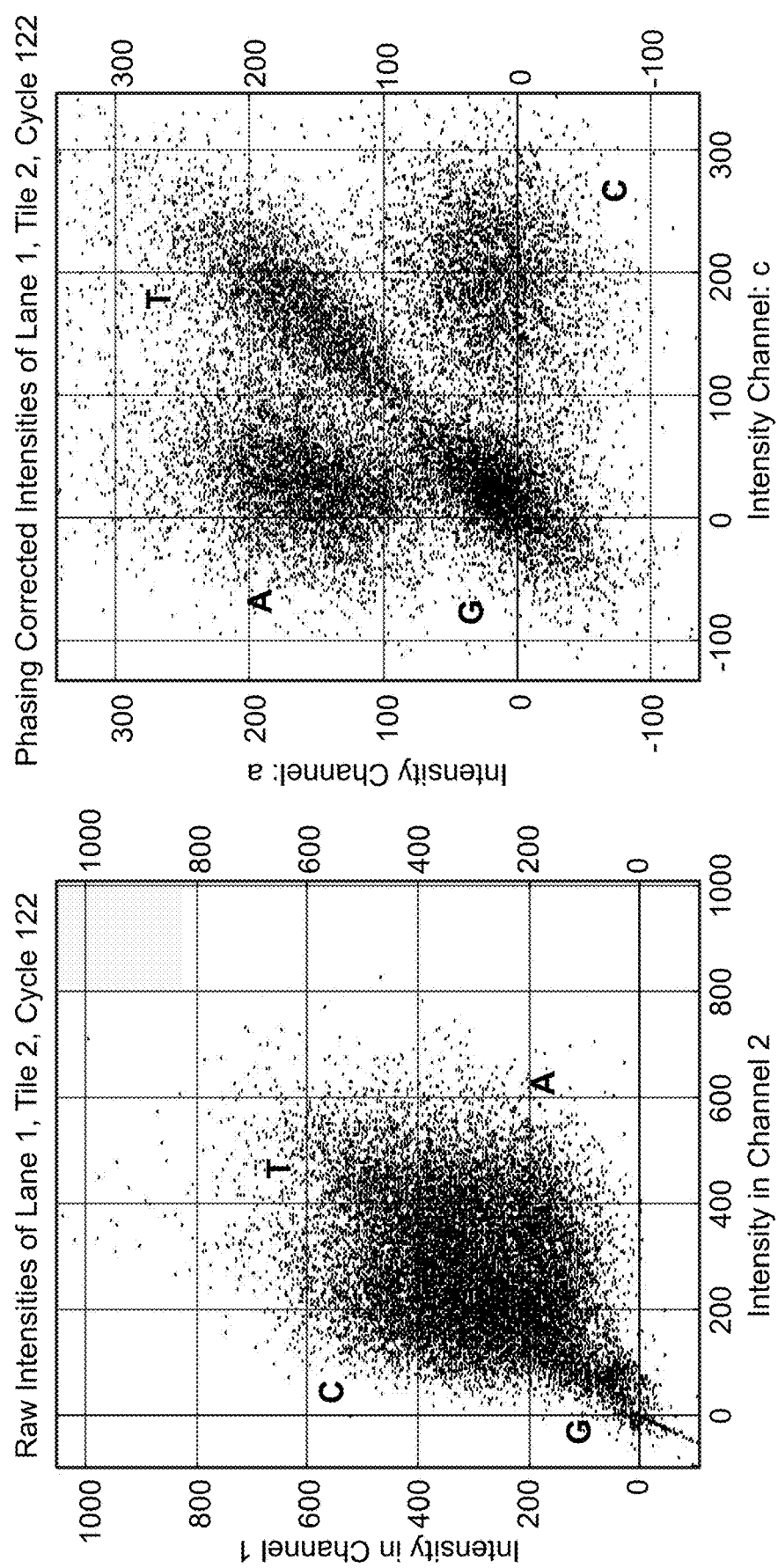
FIGS. 1A and 1B depict intensity data for a two-channel system.

The present application describes various methods and systems for carrying out the methods. Examples of some of the methods are described as a series of steps. However, it should be understood that embodiments are not limited to the particular steps and/or order of steps described herein. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other embodiments.

The analysis of image data presents a number of challenges, especially with respect to comparing images of an item or structure that are captured from different points of reference. Most image analysis methodology employs, at least in part, steps for aligning multiple separate images with respect to each other based on characteristics or elements present in both images. Various embodiments of the compositions and methods disclosed herein improve upon previous methods for image analysis. Some previous methods for image analysis are set forth in U.S. Patent Application Publication No. 2012/0020537 filed on Jan. 13, 2011 and entitled, "DATA PROCESSING SYSTEM AND METHODS," the content of which is incorporated herein by reference in its entirety. Embodiments described hereinafter are also described in U.S. Provisional Application No. 61/911,319, filed on Dec. 3, 2013, which is incorporated herein by reference in its entirety. One or more embodiments may also be used with embodiments described in U.S. Provisional Application No. 62/052,189, filed on Sep. 18, 2014, which is incorporated herein by reference in its entirety.

Recently, tools have been developed that acquire and analyze image data generated at different time points or perspectives. Some examples include tools for analysis of satellite imagery and molecular biology tools for sequencing and characterizing the molecular identity of a specimen. In any such system, acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. As such, methods and systems which improve the speed and accuracy of analysis of the acquisition and analysis of image data would be beneficial.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the embodiments of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year, and can now reach hundreds of gigabases in a single run of a DNA sequencing device. If computational infrastructure requirements grew proportionately, large genome-scale experiments would remain out of reach to most researchers. Thus, the generation of more raw sequence data will increase the need for secondary analysis and data storage, making optimization of data transport and storage extremely valuable. Some embodiments of the methods and systems presented herein can reduce the time, hardware, networking, and laboratory infrastructure requirements needed to produce usable sequence data.

As used herein, a "feature" is an area of interest within a specimen or field of view. When used in connection with microarray devices or other molecular analytical devices, a feature refers to the area occupied by similar or identical molecules. For example, a feature can be an amplified oligonucleotide or any other group of a polynucleotide or polypeptide with a same or similar sequence. In other embodiments, a feature can be any element or group of elements that occupy a physical area on a specimen. For example, a feature could be a parcel of land, a body of water or the like. When a feature is imaged, each feature will have some area. Thus, in many embodiments, a feature is not merely one pixel.

The distances between features can be described in any number of ways. In some embodiments, the distances between features can be described from the center of one feature to the center of another feature. In other embodiments, the distances can be described from the edge of one feature to the edge of another feature, or between the outer-most identifiable points of each feature. The edge of a feature can be described as the theoretical or actual physical boundary on a chip, or some point inside the boundary of the feature. In other embodiments, the distances can be described in relation to a fixed point on the specimen or in the image of the specimen.

Multiple copies of nucleic acids at a feature can be sequenced, for example, by providing a labeled nucleotide base to the array of molecules, thereby extending a primer hybridized to a nucleic acid within a feature so as to produce a signal corresponding to a feature comprising the nucleic acid. In preferred embodiments, the nucleic acids within a feature are identical or substantially identical to each other.

In some of the image analysis methods described herein, each image in the set of images includes colors signals, wherein a different color corresponds to a different nucleotide base. In some aspects, each image of the set of images comprises signals having a single color selected from at least four different colors. In certain aspects, each image in the set of images comprises signals having a single color selected from four different colors.

With respect to certain four-channel methods described herein, nucleic acids can be sequenced by providing, four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, such methods can further comprise providing additional labeled nucleotide bases to the array of molecules, thereby producing a plurality of cycles of color images.

With respect to certain two-channel methods described herein, nucleic acids can be sequenced utilizing methods and systems described in U.S. Patent Application Publication No. 2013/0079232, the disclosure of which is incorporated herein by reference in its entirety. As a first example, a nucleic acid can be sequenced by providing a first nucleotide type that is detected in a first channel, a second nucleotide type that is detected in a second channel, a third nucleotide type that is detected in both the first and the second channel and a fourth nucleotide type that lacks a label that is not, or minimally, detected in either channel. In certain aspects, such methods can further comprise providing additional labeled nucleotide bases to the array of molecules, thereby producing a plurality of cycles of color images.

Quality Scoring

Quality scoring refers to the process of assigning a quality score to each base call. In some embodiments where four different nucleotides are detected using fewer than four different labels, base calling requires a different set of analytical approaches compared to systems using traditional four-label detection. As an example, SBS can be performed utilizing two-channel methods and systems described in U.S. Patent Application Publication No. 2013/0079232, the content of which is incorporated herein by reference in its entirety. For example, in embodiments that make use of two-channel detection, base calling is performed by extracting image data from two images, rather than four. Because of the fundamental differences involved in two-channel base calling, traditional quality scoring approaches as applied to four channel base calling is not compatible with two-channel base call data. For example, the error profile presented by two-channel data is fundamentally different from the error profile of four-channel data. In view of these differences, a new approach for evaluating the quality of a base call is required.

Accordingly, presented herein are methods and systems for evaluating the quality of a base call from a sequencing read. In some embodiments, the sequencing read utilizes two-channel base calling. In some embodiments, the sequencing read utilizes one-channel base calling.

The quality score is typically quoted as QXX where the XX is the score and it means that that particular call has a probability of error of 10(−XX/10). For example Q30 equates to an error rate of 1 in 1000, or 0.1% and Q40 equates to an error rate of 1 in 10,000 or 0.01%.

In some embodiments, a quality table is generated using Phred scoring on a calibration data set, the calibration set being representative of run and sequence variability. Phred scoring is described in greater detail in U.S. Pat. No. 8,392,126 entitled, "METHOD AND SYSTEM FOR DETERMINING THE ACCURACY OF DNA BASE IDENTIFICATIONS," the content of which is incorporated herein by reference in its entirety.

In some embodiments, the methods can comprise the steps of: (a) calculating a set of predictor values for the base call; (b) using the predictor values to look up a quality score in a quality table. In certain embodiments, quality scoring is performed by calculating a set of predictors for each base call, and using those predictor values to look up the quality score in a quality table. In some embodiments, the quality table is generated using a modification of the Phred algorithm on a calibration data set representative of run and sequence variability. The predictor values for each base call can be any suitable aspect that may indicate or predict the quality of the base call in a given sequencing run. For example, some suitable predictors are set forth in U.S. Patent Application Publication No. 2012/0020537 filed on Jan. 13, 2011 and entitled, "DATA PROCESSING SYSTEM AND METHODS," the content of which is incorporated herein by reference in its entirety. As described in greater detail hereinbelow, suitable predictor values can include, for example: online overlap; purity; phasing; start5; hexamer score; motif accumulation; endiness; approximate homopolymer; intensity decay; penultimate chastity; signal overlap with background (SOWB); and shifted purity G adjustment. Any suitable combination of the above predictor values can be used in the methods presented herein.

In certain embodiments, the quality predictors used in the Phred algorithm include online overlap; purity; phasing; start5; hexamer score; motif accumulation; endiness; approximate homopolymer; intensity decay; penultimate chastity; and signal overlap with background (SOWB).

As used herein, "online overlap" refers to a measurement of the separation between the foreground called intensities and the background intensities. For example, in some embodiments, this score is a statistic measuring the signal to noise of the read up to the scored base call, and is weighted to account more for the last few base calls, although even the first base calls in the read have an influence.

As used herein, "purity" refers to a measurement that captures how reliable a base call is likely to be based only on the current cycle, and measures how significant the called base is when compared to the other three bases.

As used herein, "phasing" refers to a measurement of the noise carried over from the previous and the next cycles, which is essentially the sum of phasing and pre-phasing weights.

As used herein, "Start5" refers to a binary metric that captures the sample preparation fragmentation at the beginning of a read. For example, in an exemplary embodiment, this predictor can receive a binary score of "1" during the first 5 cycles, and "0" for every cycle thereafter.

As used herein, "hexamer score" refers to a measurement that examines hexamers and returns an enrichment factor that reflects how much the hexamer is enriched near sequence specific errors. For example, in some embodiments, this score associates a measure of sequencing difficulty to every six-base sequence and is applied starting at cycle 6 of the run. Thus, the values applied before cycle 6 are the mean value of the predictor when all hexamers are averaged together.

As used herein, "motif accumulation" refers to a measurement that maintains a cumulative sum of the Hexamer Score predictor, accounting for how difficult the sequence context has been in the prior cycles of the read. For example, in some embodiments, this score is the cumulative sum of the hexamer score and is intended to measure the overall difficulty of the sequencing read up to the scored base call.

As used herein, "endiness" refers to a measurement that tracks how close the read is to completion. For example, in some embodiments, this score is the reciprocal of the cycle number.

As used herein, "approximate homopolymer" refers to a calculation of the number of consecutive identical base calls preceding a base call. In certain embodiments, the calculation can allow one exception, in order to identify problematic sequence contexts such as homopolymer runs and problematic motifs such as "GGCGG".

As used herein, "intensity decay" refers to the identification of base calls that suffer loss of signal as sequencing progresses. For example, this can be done by comparing the brightest intensity at the current cycle to the brightest intensity at cycle 1.

As used herein, "penultimate chastity" refers to a measurement of early read quality in the first 25 bases based on the second worst chastity value. For example, in some embodiments, this score is related to the read quality, which is correlated with the overall level of quality in the first 25 cycles. This predictor is very similar to the criteria used to mark a read as filtered or unfiltered, and has the effect of making the quality scores agnostic as to whether all data from a run is analyzed or only the data passing filter. Chastity can be determined as the highest intensity value divided by the sum of the highest intensity value and the second highest intensity value, where the intensity values are obtained from four color channels. For example, in some embodiments, methods of quality evaluation can further include identifying reads where the second worst chastity in the first subset of base calls is below a threshold, and marking those reads as poor quality data. The first subset of base calls can be any suitable number of base calls which provides a sufficient For example, the subset can be the first 1, 2, 3, 4, 5, 6, 7, 8, 9, 10, 11, 12, 13, 14, 15, 16, 17, 18, 19, 20, 21, 22, 23, 24, 25 or greater than the first 25 base calls. This can be termed read filtering, such that in certain embodiments, clusters that meet this cutoff are referred to as having "passed filter".

As used herein, "signal overlap with background" (SOWB) refers to a measurement of the separation of the signal from the noise in previous and subsequent cycles. In a preferred embodiment, the measurement utilizes the 5 cycles immediately preceding and following the current cycle.

As used herein, "Shifted Purity G adjustment" refers to a measurement of the separation of the signal from the noise for the current base call only, while also accounting for G quenching effects. Due to an interaction between the dye and the DNA base incorporated in the previous cycle, the intensities in certain color channels may be decreased (quenched) in cycles following those cycles where a G nucleotide was incorporated.

After calculating quality scores, additional operations can optionally be performed. Thus, in some embodiments, the method for evaluating the quality of a base call further comprises discounting unreliable quality scores at the end of each read. In preferred embodiments, the step of discounting unreliable quality scores comprises using an algorithm to identify a threshold of reliability. In a more preferred embodiment, reliable base calls comprise q-values above the threshold and unreliable base calls comprise q-values below the threshold. An algorithm for determining a threshold of reliability can comprise the End Anchored Maximal Scoring Segments (EAMSS) algorithm, for example. As used herein, an "EAMSS algorithm" is an algorithm that identifies transition points where good and reliable base calls (with mostly high q-values) become unreliable base calls (with mostly low q-values). The identification of such transition points can be done, for example, using a Hidden Markov Model that identifies shifts in the local distributions of quality scores. For example, a Hidden Markov Model can be used. Useful Hidden Markov Models are described, for example, in Lawrence R. Rabiner (February 1989). "A tutorial on Hidden Markov Models and selected applications in speech recognition". Proceedings of the IEEE 77 (2): 257-286. doi: 10.1109/5.18626. However, it will be apparent to one of skill in the art that any suitable method of discounting unreliable quality scores may be employed. In a preferred embodiment, unreliable base calls can include base calls with a strong bias toward G base calls.

Real Time Metrics

The methods and systems provided herein can also utilize real-time metrics to display run quality to a user. Metrics can be displayed as graphs, charts, tables, pictures or any other suitable display method that provides a meaningful or useful representation of some aspect of run quality to a user. For example, real-time metrics displayed to a user can include a display of intensity values over the cycles of a run, the quality of the focus of optical equipment and cluster density in each lane. Additional metrics displays can include Q score, shown as a distribution based on the Q score, or as a heat map on a per cycle basis, for example. In some embodiments, real time metrics can include a summary table of various parameters, sorted by, for example, lane, tile, or cycle number. Image data from an entire tile or subregion of a tile may be displayed for a visual confirmation of image quality. Such image data may include close-up, thumbnail images of some or all parts of an image.

Additionally, some metrics displays can include the error rate on a per-cycle basis. The error rate can be calculated using a control nucleic acid.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in U.S. Patent Application Publication No. 2013/0079232, the disclosure of which is incorporated herein by reference in its entirety. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as $\alpha$-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and $\gamma$-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

It will be appreciated that any of the above-described sequencing processes can be incorporated into the methods and/or systems described herein. Furthermore, it will be appreciated that other known sequencing processes can be easily by implemented for use with the methods and/or systems described herein. It will also be appreciated that the methods and systems described herein are designed to be applicable with any nucleic acid sequencing technology. Additionally, it will be appreciated that the methods and systems described herein have even wider applicability to any field where tracking and analysis of features in a specimen over time or from different perspectives is important. For example, the methods and systems described herein can be applied where image data obtained by surveillance, aerial or satellite imaging technologies and the like is acquired at different time points or perspectives and analyzed.

Systems

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating a set of amplicons in situ. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

Figures 2A, 2B, 2C:
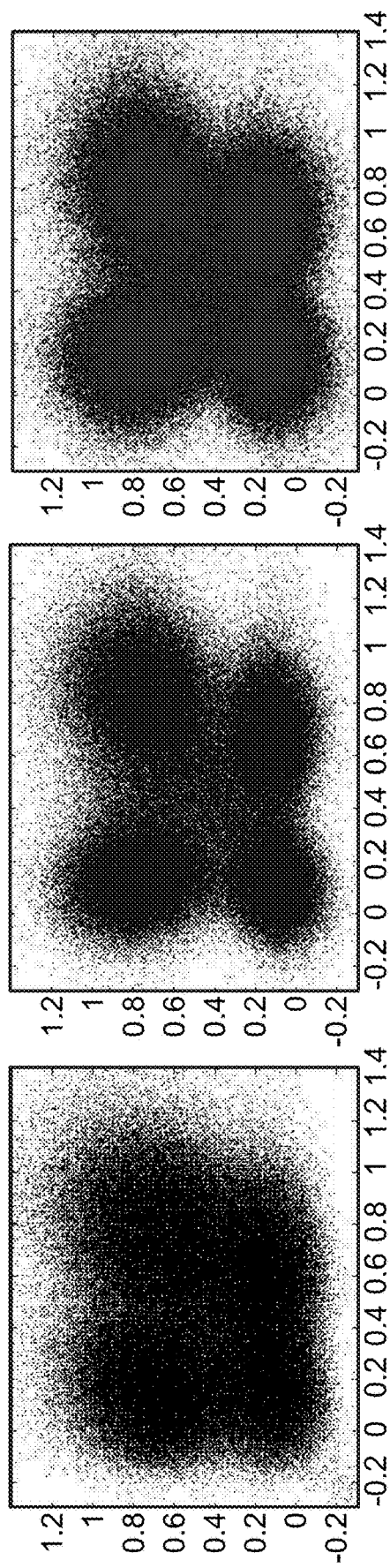
FIG. 2 depicts intensity data for a two-channel system which has been subjected to various phasing corrections.

The following description is with respect to FIGS. 1A, 1B, and 2. Embodiments described hereinafter are also described in U.S. Provisional Application No. 61/915,455, filed on Dec. 12, 2013, which is incorporated herein by reference in its entirety.

The analysis of image data presents a number of challenges, especially with respect to comparing images of an item or structure that are captured from different points of reference. Most image analysis methodology employs, at least in part, steps for aligning multiple separate images with respect to each other based on characteristics or elements present in both images. Various embodiments of the compositions and methods disclosed herein improve upon previous methods for image analysis. Some previous methods for image analysis are set forth in U.S. Patent Application Publication No. 2012/0020537 filed on Jan. 13, 2011 and entitled, "DATA PROCESSING SYSTEM AND METHODS," the content of which is incorporated herein by reference in its entirety.

Recently, tools have been developed that acquire and analyze image data generated at different time points or perspectives. Some examples include tools for analysis of satellite imagery and molecular biology tools for sequencing and characterizing the molecular identity of a specimen. In any such system, acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. As such, methods and systems which improve the speed and accuracy of analysis of the acquisition and analysis of image data would be beneficial.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the embodiments of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year, and can now reach hundreds of gigabases in a single run of a DNA sequencing device. If computational infrastructure requirements grew proportionately, large genome-scale experiments would remain out of reach to most researchers. Thus, the generation of more raw sequence data will increase the need for secondary analysis and data storage, making optimization of data transport and storage extremely valuable. Some embodiments of the methods and systems presented herein can reduce the time, hardware, networking, and laboratory infrastructure requirements needed to produce usable sequence data.

As used herein, a "feature" is an area of interest within a specimen or field of view. When used in connection with microarray devices or other molecular analytical devices, a feature refers to the area occupied by similar or identical molecules. For example, a feature can be an amplified oligonucleotide or any other group of a polynucleotide or polypeptide with a same or similar sequence. In other embodiments, a feature can be any element or group of elements that occupy a physical area on a specimen. For example, a feature could be a parcel of land, a body of water or the like. When a feature is imaged, each feature will have some area. Thus, in many embodiments, a feature is not merely one pixel.

The distances between features can be described in any number of ways. In some embodiments, the distances between features can be described from the center of one feature to the center of another feature. In other embodiments, the distances can be described from the edge of one feature to the edge of another feature, or between the outer-most identifiable points of each feature. The edge of a feature can be described as the theoretical or actual physical boundary on a chip, or some point inside the boundary of the feature. In other embodiments, the distances can be described in relation to a fixed point on the specimen or in the image of the specimen.

Multiple copies of nucleic acids at a feature can be sequenced, for example, by providing a labeled nucleotide base to the array of molecules, thereby extending a primer hybridized to a nucleic acid within a feature so as to produce a signal corresponding to a feature comprising the nucleic acid. In preferred embodiments, the nucleic acids within a feature are identical or substantially identical to each other.

In some of the image analysis methods described herein, each image in the set of images includes colors signals, wherein a different color corresponds to a different nucleotide base. In some aspects, each image of the set of images comprises signals having a single color selected from at least four different colors. In certain aspects, each image in the set of images comprises signals having a single color selected from four different colors.

With respect to certain four-channel methods described herein, nucleic acids can be sequenced by providing, four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, such methods can further comprise providing additional labeled nucleotide bases to the array of molecules, thereby producing a plurality of cycles of color images.

With respect to certain two-channel methods described herein, nucleic acids can be sequenced utilizing methods and systems described in U.S. Patent Application Publication No. 2013/0079232, the disclosure of which is incorporated herein by reference in its entirety. As a first example, a nucleic acid can be sequenced by providing a first nucleotide type that is detected in a first channel, a second nucleotide type that is detected in a second channel, a third nucleotide type that is detected in both the first and the second channel and a fourth nucleotide type that lacks a label that is not, or minimally, detected in either channel. In certain aspects, such methods can further comprise providing additional labeled nucleotide bases to the array of molecules, thereby producing a plurality of cycles of color images.

Phasing Estimation

A phasing estimation is an analytical tool for reducing noise during multiple cycles of a sequencing run. For example, in any given cycle of a sequencing run, one or more molecules may become "phased" at each cycle. As used herein, "phased", "phasing" and like terms refer to the situation where a molecule at a feature falls at least one base behind other molecules at the same feature as a result of the feature being sequenced at a particular cycle. As used herein, "pre-phased", "pre-phasing" and like terms refer to the situation where a molecule at a feature jumps at least one base ahead of other molecules at the same feature as a result of the feature being sequenced at a particular cycle. The effects of phasing and pre-phasing become more pronounced with higher phasing/prephasing rates and longer reads. Thus, in order to maintain accurate base calling over an extended number of cycles, it is important to correct for this phenomenon. The methods and systems presented herein provide a computational solution which surprisingly yield improved base calling over extended sequencing cycles compared to traditional phasing correction methods.

The methods and systems provided herein can assume that a fixed fraction of molecules at each feature become phased at each cycle, in the sense that those molecules fall one base behind in sequencing. Thus, in a preferred embodiment, a phasing estimation is performed to adjust the observed intensities in a way that reduces the noise created by phased molecules.

Traditional phasing correction can be performed by methods as described in the incorporated materials of U.S. Patent Application Publication No. 2012/0020537. As described therein, a traditional approach to phasing correction involves creating a phasing matrix to model phasing effects at any given cycle. This can be done, for example, by creating an NxN matrix where N is the total number of cycles. Then, to phase-correct intensities for a given cycle, the inverse of the phasing matrix is taken and the matrix row corresponding to the cycle is extracted. As a result, the vector of actual intensities for cycles 1 through N is the product of phasing matrix inverse and observed intensities for cycles 1 through N. As an example of such an approach, a phasing estimation is performed by calculating phasing and prephasing rates from the first 12 cycles of intensity data. Corrections derived from these rates are then applied to all cycles to improve basecalling error rates. Because phasing rates are estimated during the early part of a sequencing run, an innacurate phasing rate estimation made during early cycles (e.g., during cycles 1-12) can potentially affect the data obtained during later cycles.

For example, in traditional phasing correction methods, if the phasing rate estimation is off, basecall accuracy is affected for the entirety of a run and is not adjusted. This effect is enhanced when sequencing low diversity samples such as single amplicons. Thus, if phasing rates estimated during early cycles are based on a low diversity of bases, the rates may not accurately reflect phasing rates during later cycles of a sequencing run. Traditional phasing correction approaches are not effective in adjusting to changing phasing rates in later cycles. Additionally, traditional phasing correction approaches are not designed to estimate the phasing rate on 2 channel data.

Empirical Phasing Correction

Presented herein are improved methods of performing phasing correction. The methods described herein provide surprising advantages in comparison to the traditional phasing correction approaches described above. For example, the methods presented herein include determining phasing corrections as an ongoing analysis throughout a sequencing run. As a result of this approach, an innacurate phasing rate estimation made during early cycles (e.g., during cycles 1-12) will not adversely affect later cycles.

Presented herein is a method of performing phasing correction comprising empirical analysis. The methods presented herein are an alternative to, or can supplement traditional phasing correction analysis as described above. The methods presented herein are surprisingly effective when applied to, for example, 1-channel and 2-channel data.

In some embodiments, the methods comprise an empirical phasing correction. Particular embodiments employ the step of applying a first order phasing correction. For example, in some embodiments, the method comprises a first order phasing correction for a given cycle as defined by the following:

$$I(cycle)=I(cycle)-X*I(cycle-1)-Y*I(cycle+1)$$

where I represents intensity and X and Y represent the phasing and prephasing weights calculated for this cycle. It will be understood that, utilizing this approach, if the correct values of X and Y are chosen, then the mean chastity (quality) of intensity values are maximized. For example, it is possible to numerically optimize via a pattern search over X and Y to maximize the mean chastity. Once X and Y values are identified with maximal mean chastity, then the above correction can be applied and then basecalling can occur directly subsequent.

In some embodiments, a separate phasing correction is calculated more than once during a sequencing run. For example, in some embodiments, a separate phasing correction is calculated 2, 3, 4, 5, 6, 7, 8, 9, 10, 15, 20, 25, 30, 35, 40, 45, 50, 55, 60, 65, 70, 75, 80, 85, 90, 95, 100, or more than 100 times during a sequencing run. In some embodiments, a phasing correction is calculated at nearly every cycle during a sequencing run. In some embodiments, a phasing correction is calculated at every cycle during a sequencing run.

In some embodiments, a separate phasing correction is calculated for different locations of an imaged surface at the same cycle. For example, in some embodiments, a separate phasing correction is calculated for every individual lane of an imaged surface, such as an individual flow cell lane. In some embodiments a separate phasing correction is calculated for every subset of a lane, such as an imaging swath within a flow cell lane. In some embodiments, a separate phasing correction is calculated for each individual image, such as, for example, every tile. In certain embodiments, a separate phasing correction is calculated for every tile at every cycle.

In particular embodiments, the approach described above for empirical phasing correction serves to optimize the phasing and prephasing corrections for each cycle and tile to maximize the mean chastity of the intensity data. The result is that RTA is no longer dependent upon an accurate rate calculation, since the best correction is applied at every cycle, but instead performs cycle-by-cycle corrections that are analyzed at a later cycle, for example, cycle 25. This analysis gives a calculated rate that can be saved in a file and/or displayed in a user interface.

As set forth in FIG. 1, the effects of application of the above approach can result in a dramatic resolution of base calling. FIG. 1A shows raw intensities for a particular tile and a particular cycle in a two-channel system where the C nucleotide is represented by signal in channel 1 only, A nucleotide is represented by signal in channel 2 only, T nucleotide is represented by signal in both channels 1 and 2, and G nucleotide is "dark." FIG. 1B shows phasing corrected intensities of the same data using the above-described phasing correction. As shown in FIG. 1B, application of the above-described phasing correction approach dramatically increases resolution of intensities assigned to each of the four bases. To aid in distinguishing the data points, data for the nucleotides may be indicated in different colors. For example, the A nucleotide data may be indicated in green, the C nucleotide may be indicated in black, the T nucleotide may be indicated in pink, and the G nucleotide may be indicated in blue.

In particular embodiments, due to the physics of phasing, as reads get longer, higher order terms can become more and more important in phasing correction. Thus, in particular embodiments, to correct for this, a second order empirical phasing correction can be calculated. For example, in some embodiments, the method comprises a second order phasing correction as defined by the following:

$$I(cycle)=-a*I(cycle-2)-A*I(cycle-1)+I(cycle)-B*I(cycle+1)-b*I(cycle+2)$$

where I represents intensity and a, A, B, and b represent the first and second order terms to the phasing correction. In particular embodiments, the calculation is optimized over a, A, B, b.

In some embodiments, higher order terms can be used to correct for high phasing and/or prephasing rates. In particular embodiments, the higher the phasing and/or prephasing rates, the bigger the difference the higher order terms make. In particular embodiments, the higher the phasing and/or prephasing rates and the longer the read, the more important the higher order terms become.

The methods provided herein are superior and provide significant advantages over traditional phasing correction approaches. For example, unlike traditional methods, there is no requirement to accurately estimate a phasing rate in the first 10 cycles of a run. Further, unlike traditional methods, there is no requirement to aggregate phasing estimates across tiles to arrive at phasing correction that is generalized across all tiles. In addition, unlike traditional methods where a phasing correction is derived and applied to all cycles, in the methods presented herein, cycle to cycle corrections are independent. Specifically, permanent error is not introduced into the phasing correction algorithm by a few cycles of bad data.

The methods presented herein are particularly unaffected by low diversity runs. For example, in sequencing runs where only one or a very few sequences are being determined, such as in single amplicon or in metagenomic applications, the phasing correction is not entirely dependent on the accuracy of a calculation made based on a limited set of early cycles, and instead can optimize phasing corrections for each tile and each cycle.

Although the methods and systems presented herein are exemplified primarily in the context of two-channel sequencing data, it should be appreciated that the same methods and algorithms can be directly applied to 4 channel data with substantially reduced error rates in increased alignment scores. An example of phasing correction calculations using 2 channel data is presented below as Example 1. An example of phasing correction calculations using 4 channel data is presented below as Example 2.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in U.S. Patent Application Publication No. 2013/0079232, the disclosure of which is incorporated herein by reference in its entirety. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

Systems

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating a set of amplicons in situ. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

It will be appreciated that any of the above-described sequencing processes can be incorporated into the methods and/or systems described herein. Furthermore, it will be appreciated that other known sequencing processes can be easily by implemented for use with the methods and/or systems described herein. It will also be appreciated that the methods and systems described herein are designed to be applicable with any nucleic acid sequencing technology. Additionally, it will be appreciated that the methods and systems described herein have even wider applicability to any field where tracking and analysis of features in a specimen over time or from different perspectives is important. For example, the methods and systems described herein can be applied where image data obtained by surveillance, aerial or satellite imaging technologies and the like is acquired at different time points or perspectives and analyzed.

EXAMPLES

Example 1

Empirical Phasing Correction On 2 Channel Data

Empirical phasing was implemented in a 2 channel sequencing system running whole genome sequencing of human samples. FIG. 1 shows representative data from a particular tile and a particular cycle. Specifically, as shown in FIG. 1B, by using the phasing correction method described below, a dramatically increased resolution results for intensities assigned to each of the four bases.

The fundamental idea of the empirical correction algorithm is that phasing correction maximizes the cumulative chastity of the data. Using the correction algorithm described above, it is possible to iterate over all phasing correction values and establish which gives the best results. An example is set forth in FIG. 2, which depicts intensity data for a two-channel system which has been subjected to various phasing corrections. On the left is cycle 150 from the sequencing run, where phasing is under-corrected. In the middle is the optimally corrected data. On the right is overcorrected data. Clearly, the mean chastity of the data is maximized when the assumed phasing rate is the true value.

This knowledge can be leveraged to estimate a phasing and pre-phasing correction parameter at every cycle which maximizes the chastity for that cycle. To accomplish this, a first order phasing correction is implemented:

$$I(\text{cycle})=I(\text{cycle})-A*I(\text{cycle}-1)-B*I(\text{cycle}+1)$$

Normally, the constants A and B are calculated from the estimates phasing/pre-phasing rates and weighted by the cycle number. In an embodiment using empirical phasing correction, the method can optimize over A and B at every cycle using a pattern search. The cost function is the number of clusters that fail a chastity filter. Thus, A and B are selected to maximize the data quality.

To minimize the computational cost of effectively correcting at many different phasing rates, then choosing the best one, the optimal A and B values at every cycle were saved in the following file:
\Data\Intensities BaseCalls\Phasing EmpiricalPhasingCorrection_lane_read_tile.txt.

These data files have the following structure:
Cycle PhasingCorrection PrephasingCorrection
To determine the phasing or pre-phasing rate, the list of PhasingCorrection was plotted by cycle. The phasing rate is the slope of the resulting line.

Example 2

Empirical Phasing Correction On Low Diversity 4 Channel Data

Four channel sequencing of low diversity samples such as single amplicons presents several challenges, including low throughput, low % PF, and low quality scores. Even when a known phage genome (PhiX) was spiked into the sample up to levels approaching 50%, these challenges persist.

A single amplicon sequencing run was performed utilizing empirical phasing correction to give high quality data under extremely low diversity conditions. In this experiment, 3 separate single amplicon runs were performed with paired end runs of 101 cycles from each end. A version of real time analysis software (RTA version 1.17.23) was used to analyze the four channel data. This RTA version included empirical phasing. In all experiments, all cluster densities were greater than 1000 k/mm$^2$ and the number of clusters passing filter was greater than 90%. All sequencing data had a percent quality score above Q30 of 93%. These results demonstrate that empirical phasing on low diversity sequencing data yields superior data quality.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

Figure 3:
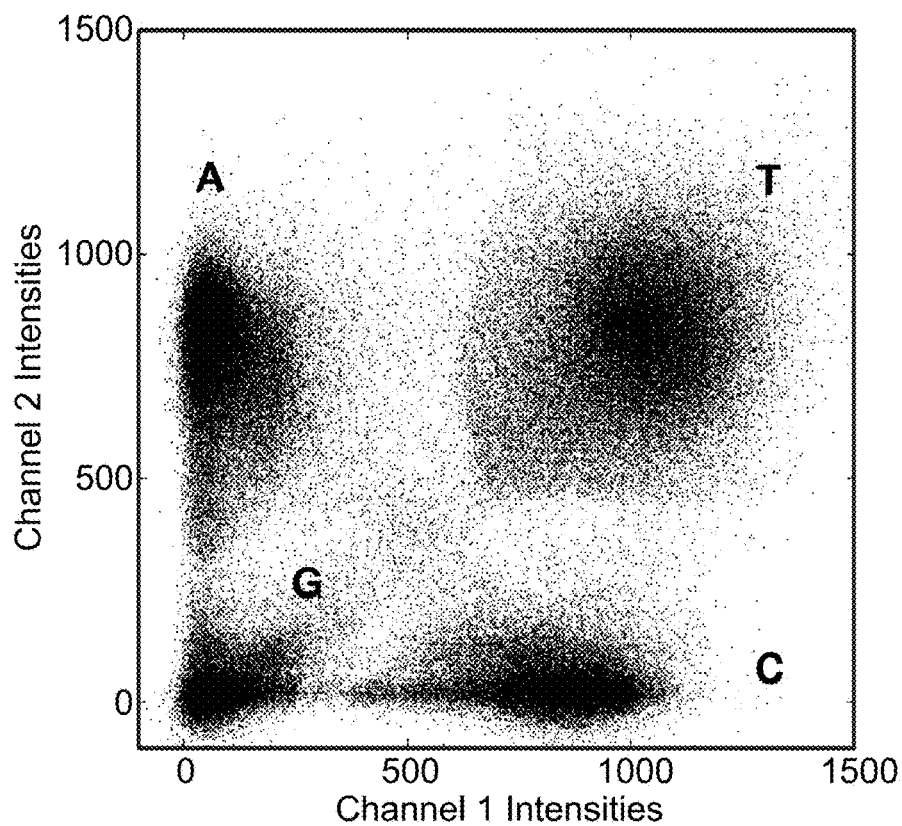
FIG. 3 shows an exemplary plot of image intensities from two channel sequencing.
Figure 4:
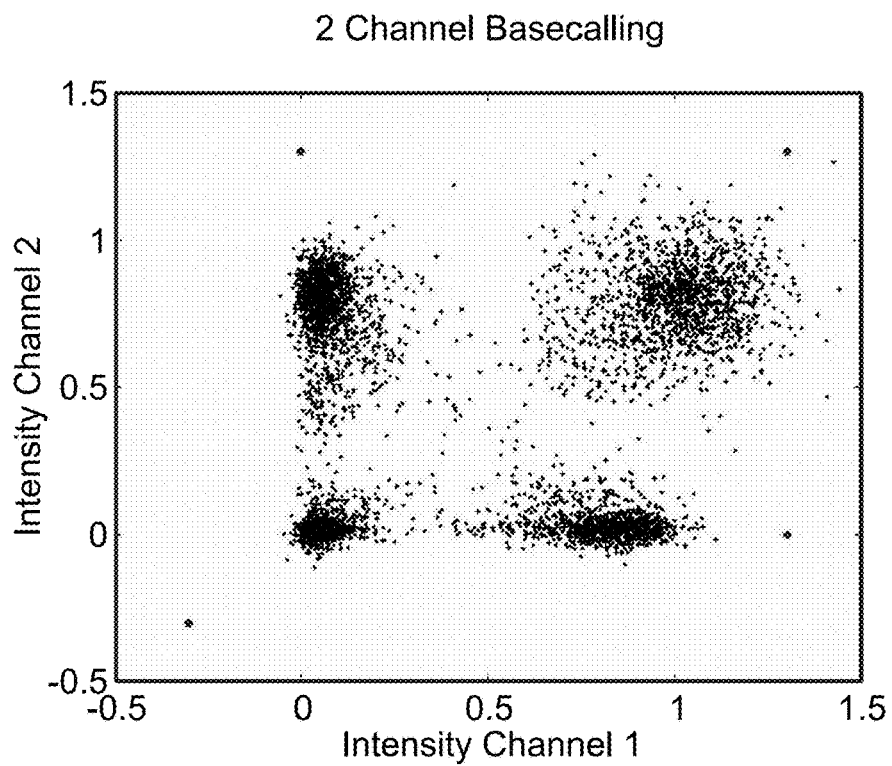
FIG. 4 shows an approach to fit Gaussian distributions to two-channel intensity data, according to one embodiment.
Figure 5A:
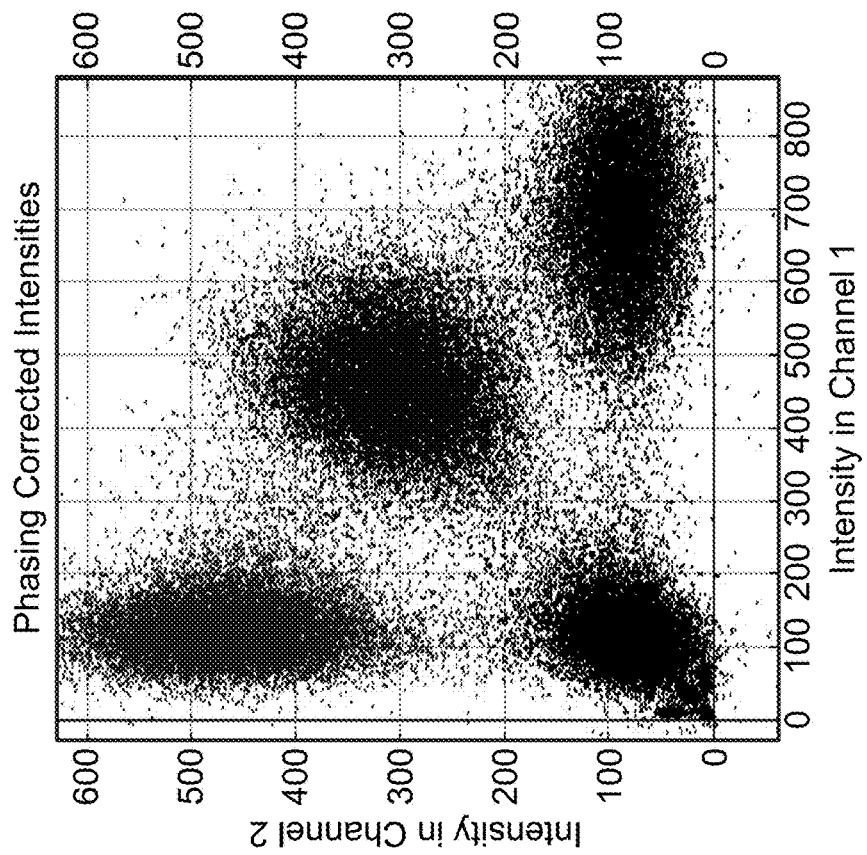
FIG. 5 sets forth application of Expectation Maximization to one-channel sequencing data (left image) and two-channel sequencing data (right image).
Figure 5B:
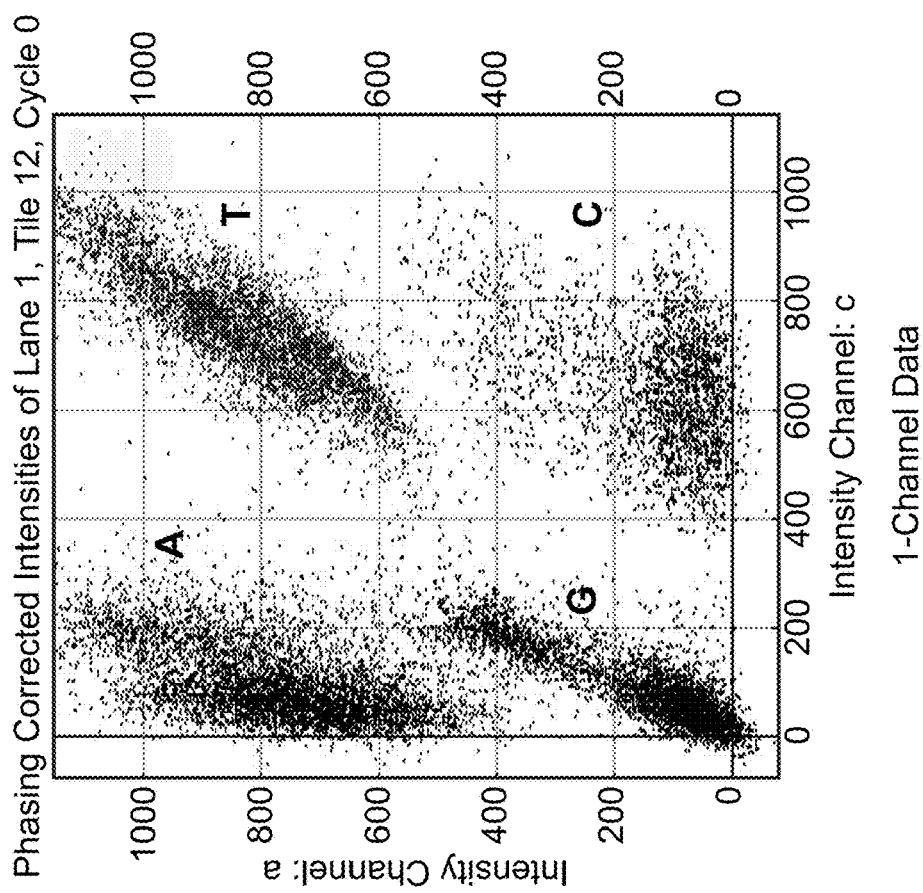

The following description is with respect to FIGS. 3-5. Embodiments described hereinafter are also described in U.S. Provisional Application No. 61/915,426, filed on Dec. 12, 2013, which is incorporated herein by reference in its entirety.

The analysis of image data presents a number of challenges, especially with respect to comparing images of an item or structure that are captured from different points of reference. Most image analysis methodology employs, at least in part, steps for aligning multiple separate images with respect to each other based on characteristics or elements present in both images. Various embodiments of the compositions and methods disclosed herein improve upon previous methods for image analysis. Some previous methods for image analysis are set forth in U.S. Patent Application Publication No. 2012/0020537 filed on Jan. 13, 2011 and entitled, "DATA PROCESSING SYSTEM AND METHODS," the content of which is incorporated herein by reference in its entirety.

Recently, tools have been developed that acquire and analyze image data generated at different time points or perspectives. Some examples include tools for analysis of satellite imagery and molecular biology tools for sequencing and characterizing the molecular identity of a specimen. In any such system, acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. As such, methods and systems which improve the speed and accuracy of analysis of the acquisition and analysis of image data would be beneficial.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the embodiments of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year, and can now reach hundreds of gigabases in a single run of a DNA sequencing device. If computational infrastructure requirements grew proportionately, large genome-scale experiments would remain out of reach to most researchers. Thus, the generation of more raw sequence data will increase the need for secondary analysis and data storage, making optimization of data transport and storage extremely valuable. Some embodiments of the methods and systems presented herein can reduce the time, hardware, networking, and laboratory infrastructure requirements needed to produce usable sequence data.

As used herein, a "feature" is an area of interest within a specimen or field of view. When used in connection with microarray devices or other molecular analytical devices, a feature refers to the area occupied by similar or identical molecules. For example, a feature can be an amplified oligonucleotide or any other group of a polynucleotide or polypeptide with a same or similar sequence. In other embodiments, a feature can be any element or group of elements that occupy a physical area on a specimen. For example, a feature could be a parcel of land, a body of water or the like. When a feature is imaged, each feature will have some area. Thus, in many embodiments, a feature is not merely one pixel.

The distances between features can be described in any number of ways. In some embodiments, the distances between features can be described from the center of one feature to the center of another feature. In other embodiments, the distances can be described from the edge of one feature to the edge of another feature, or between the outer-most identifiable points of each feature. The edge of a feature can be described as the theoretical or actual physical boundary on a chip, or some point inside the boundary of the feature. In other embodiments, the distances can be described in relation to a fixed point on the specimen or in the image of the specimen.

Multiple copies of nucleic acids at a feature can be sequenced, for example, by providing a labeled nucleotide base to the array of molecules, thereby extending a primer hybridized to a nucleic acid within a feature so as to produce a signal corresponding to a feature comprising the nucleic acid. In preferred embodiments, the nucleic acids within a feature are identical or substantially identical to each other.

In some of the image analysis methods described herein, each image in the set of images includes colors signals, wherein a different color corresponds to a different nucleotide base. In some aspects, each image of the set of images comprises signals having a single color selected from at least four different colors. In certain aspects, each image in the set of images comprises signals having a single color selected from four different colors.

With respect to certain four-channel methods described herein, nucleic acids can be sequenced by providing, four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, such methods can further comprise providing additional labeled nucleotide bases to the array of molecules, thereby producing a plurality of cycles of color images.

With respect to certain two-channel methods described herein, nucleic acids can be sequenced utilizing methods and systems described in U.S. Patent Application Publication No. 2013/0079232, the disclosure of which is incorporated herein by reference in its entirety. As a first example, a nucleic acid can be sequenced by providing a first nucleotide type that is detected in a first channel, a second nucleotide type that is detected in a second channel, a third nucleotide type that is detected in both the first and the second channel and a fourth nucleotide type that lacks a label that is not, or minimally, detected in either channel. In certain aspects, such methods can further comprise providing additional labeled nucleotide bases to the array of molecules, thereby producing a plurality of cycles of color images.

Base Calling

Presented herein are methods and systems for identifying a nucleotide base in a nucleic acid sequence, or "base calling." Base calling refers to the process of determining a base call (A, C, G, T) for every feature of a given tile at a specific cycle. As an example, SBS can be performed utilizing two-channel methods and systems described in the incorporated materials of U.S. Patent Application Publication No. 2013/0079232. For example, in embodiments that make use of two-channel detection, base calling is performed by extracting image data from two images, rather than four. Because of the fundamental differences involved in two-channel base calling, traditional base calling approaches as applied to four channel detection is not compatible with two-channel data. In view of these differences, a new approach for base calling is required. Accordingly, presented herein are methods and systems for base calling in a 2-channel system. In some embodiments, the methods comprise iteratively fitting four Gaussian distributions to intensity data from two channels. When signals from channel 1 are plotted against signals from channel 2, signal intensity typically segregates into four general populations of intensity. As shown in FIG. 3, data from a 2 channel sequencing system can be plotted as intensity values from channel 1 (x-axis) versus intensity values from channel 2 (y-axis). In typical embodiments, one of the four nucleotides is unlabeled (dark), such as "G" nucleotide shown in FIG. 3, which has near zero signal in both channel 1 and channel 2. The signals from a certain portion of the data points are clustered near the zero point in each axis. Likewise, the signals from a certain portion of the data points labeled with one or both labels (shown as "C", "A", and "T" nucleotides in FIG. 3) form identifiable populations when plotted in a two-dimensional graph such as the one shown in FIG. 3. Thus, for example, unlike four-channel sequencing data, the intensity itself of a particular label does not encode the base. Rather, the combination of intensities, [on, off], [off, on], [on, on], [off, off], provide the encoding information for the base identity. The methods and systems presented herein provide a tool for identifying the base associated with any one particular data point in such data sets. An objective of the methods and systems presented herein is to separate the four populations as accurately as possible.

Classifiers

In some embodiments presented herein, base calling is performed by fitting a mathematical model to a set of intensity data. Any suitable mathematical model can be used in the methods presented herein in order to fit the intensity data to a set of distributions. Mathematical models that can be used in the methods presented herein can include classifiers such as, for example, a k-means clustering algorithm, a k-means-like clustering algorithm, expectation maximization, a histogram based method, and the like.

For example, in certain embodiments, one or more Gaussian distributions are fitted to a set of intensity data. In certain embodiments, 4 Gaussian distributions are fit to a set of two-channel intensity data such that one distribution is applied for each of the four nucleotides represented in the data set. In certain embodiments, intensity values can be normalized prior to fitting a Gaussian distribution. For example, as shown in the exemplary embodiment represented by FIG. 4, intensity values are normalized so that $5^{th}$ and $95^{th}$ percentiles have values of 0 and 1, respectively. Four Gaussian distributions are then fit to the data using an algorithm such as, for example an expectation maximization (EM) clustering algorithm. EM algorithms are known in the art and are useful tools to construct statistical models of the underlying data source and naturally generalize to cluster databases containing both discrete-valued and continuous-valued data. Thus, for example, in certain embodiments, an EM algorithm is applied to iteratively maximize the likelihood of observing the given data. For example, an EM algorithm is applied to iteratively maximize this likelihood over the mean and covariance for each of the Gaussian distributions. In certain embodiments, a subset of the data points in a data set is included in the calculation. Additionally or alternatively, in certain embodiments, all or substantially all data points in the data set are included in the calculation.

As a result of the EM algorithm, for each X, Y value (referring to each of the two channel intensities respectively) a value can be generated which represents the likelihood that a certain X, Y intensity value belongs to one of the four distributions. In an embodiment where four bases give four separate distributions, each X, Y intensity value will also have four associated likelihood values, one for each of the four bases. The maximum of the four likelihood values indicates the base call. Thus, as shown in the exemplary embodiment represented by FIG. 5, intensity values for a two-channel data set are assigned a base call after performing a Gaussian fit to the data set. Each data point in the graphs in FIG. 5 has a color associated with the assigned base call, which represents the maximum of the likelihood prediction values. A comparison of the base call data shown in the two graphs in FIG. 5 indicates that the base calling methods presented herein are highly accurate and are robust to varying types of sequencing chemistry. For example, the left panel of FIG. 5 is an example of chemistry that forms four intensity distributions forming a square when the intensity values are plotted. In contrast, the intensity plot in the right panel has four intensity distributions that fall within a triangle, based on the lesser intensities of the dual-labeled nucleotide. In both types of chemistry, the base calling methods presented herein provide accurate base calls.

In embodiments of the methods presented herein, a quality score can also be generated based on the Gaussian distribution approach to base calling. For example, the distance of a point to the center of the "called" distribution gives a measure of the purity of the base call. Specifically, the closer a data point lies to the center of the distribution for the called base, the greater the likelihood that the base call is accurate. Any suitable method to calculate and express the relationship between distance to the center and the likely purity of the base call can be used in the methods provided herein. In some embodiments, the quality or purity of the base call for a given data point can be expressed as the distance to the nearest centroid divided by the sum of all distances to each of the other three centroids. In some embodiments, the quality or purity of the base call for a given data point can be expressed as the distance to the nearest centroid be divided by the distance to the second nearest centroid, as described below regarding chastity filtering.

Chastity Filtering

Also presented herein are methods of filtering clusters having poor quality. The term filtering as used in relation to clusters and basecalling refers to discarding or disregarding the cluster as a data point. Thus, any clusters of poor intensity or quality can be filtered and are not included in an output data set. In certain embodiments, cluster quality is determined by a metric termed chastity. Chastity for two-channel basecalling takes on a separate meaning from the use of the term in four-channel basecalling. For example, as described in the incorporated materials of U.S. Patent Application Publication No. 2012/0020537, chastity is defined in terms of intensity of a cluster ("spot") relative to a nearby spot), and can be calculated as the highest intensity value divide by the sum of the highest intensity value and the second highest intensity value, where the intensity values are obtained from four color channels. However, because two-channel basecalling typically utilizes unlabeled nucleotides that emit very low or no signal, traditional chastity determinations are unsuitable for two-channel basecalling.

Thus, some embodiments of the present disclosure relate to determining chastity of a cluster as a function of relative distances to Gaussian centroids. In some embodiments, clusters that are not close enough to one particular Gaussian centroid in a given number of cycles are given a low chastity value and are filtered out. For example, in one specific embodiment, chastity can be calculated using the expression:

$$chastity = 1 - D1/(D1 + D2),$$

where D1 is the distance to the nearest Gaussian centroid, and D2 is the distance to the next nearest centroid. Methods of fitting Gaussian distributions to a two-channel data set are described hereinabove in the section describing basecalling methods.

In some embodiments, filtering of low-chastity clusters takes place at one or more discrete points during a sequencing run. In some embodiments, filtering occurs during template generation. Alternatively or additionally, in some embodiments, filtering occurs after a predefined cycle. In certain embodiments, filtering occurs at or after cycle 1, 2, 3, 4, 5, 6, 7, 8, 9, 10, 11, 12, 13, 14, 15, 16, 17, 18, 19, 20, 21, 22, 23, 24, 25, 26, 27, 28, 29, or after cycle 30 or later. In typical embodiments, filtering occurs at cycle 25, such that clusters that are not close enough to a Gaussian centroid in the first 25 cycles are filtered out.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

Systems

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating a set of amplicons in situ. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

It will be appreciated that any of the above-described sequencing processes can be incorporated into the methods and/or systems described herein. Furthermore, it will be appreciated that other known sequencing processes can be easily by implemented for use with the methods and/or systems described herein. It will also be appreciated that the methods and systems described herein are designed to be applicable with any nucleic acid sequencing technology. Additionally, it will be appreciated that the methods and systems described herein have even wider applicability to any field where tracking and analysis of features in a specimen over time or from different perspectives is important. For example, the methods and systems described herein can be applied where image data obtained by surveillance, aerial or satellite imaging technologies and the like is acquired at different time points or perspectives and analyzed.

EXAMPLES

Example 1

Base Calling Using Gaussian Distribution On 2 Channel Data

Base calling is performed in a 2 channel sequencing system running whole genome sequencing of human samples. After template generation, intensity values are generated for two separate imaging channels. The intensity values are normalized so that the $5^{th}$ and $95^{th}$ percentiles occur at 0 and 1, and four Gaussian distributions are fit to the data using an Expectation Maximization algorithm. A centroid (mean X,Y value) for each of the four distributions corresponding to each of the four nucleotides is calculated.

Basecalling for each cluster occurs by measuring the likelihood value calculated, which is the likelihood thatthe cluster is belonging to each of the four distributions. The centroid associated with the maximum likelihood value is selected as the basecall. This basecall process is performed for each of the clusters in the data set for each cycle.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

Figure 6:
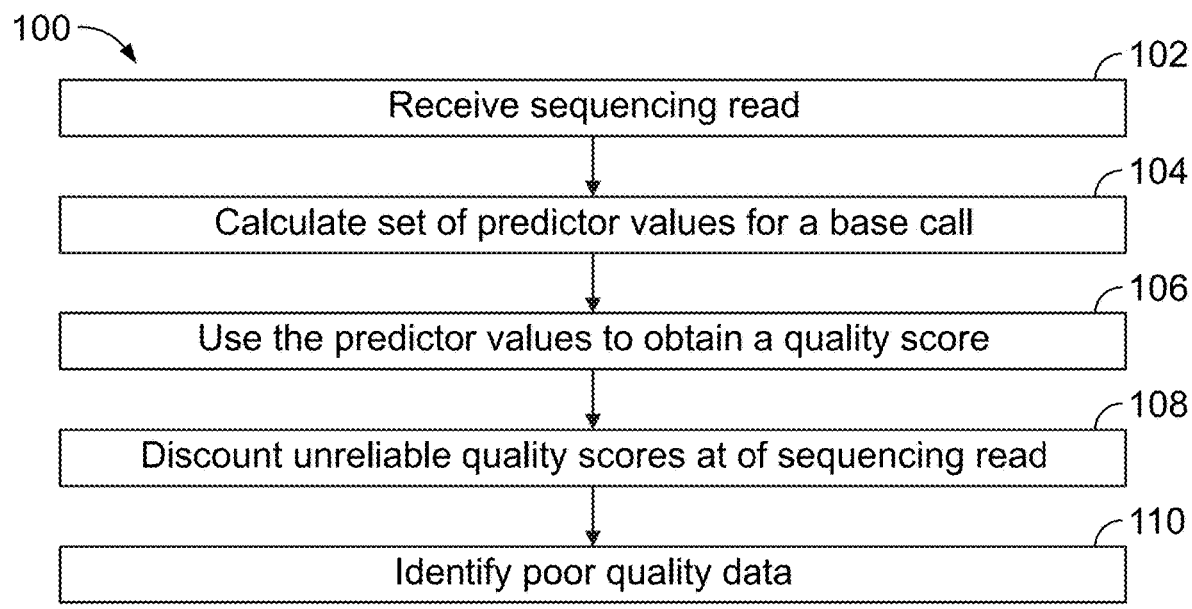
FIG. 6 is a flow chart illustrating a method in accordance with an embodiment.

FIGS. 6-9 include flowcharts that illustrate one or more methods. FIG. 6 illustrates a method 100 in accordance with an embodiment. The method 100 may be, for example, a method of evaluating the quality of a base call from a sequencing read. The method 100 may include receiving, at 102, a sequencing read having a number of base calls. The method 100 may also include calculating, at 104, a set of predictor values for a base call and using, at 106, the predictor values to look up a quality score (or similar metric) in a quality table (or database).

In one aspect, the sequencing read utilizes two-channel base calling.

In another aspect, the sequencing read utilizes one-channel base calling.

In another aspect, the quality table is generated using Phred scoring on a calibration data set. The calibration set is representative of run and sequence variability. In some embodiments, the method 100 may include generating the quality table.

In another aspect, the predictor values are selected from the group consisting of: online overlap; purity; phasing; start5; hexamer score; motif accumulation; endiness; approximate homopolymer; intensity decay; penultimate chastity; and signal overlap with background (SOWB). In particular embodiments, the set of predictor values comprises online overlap; purity; phasing; and start5. In particular embodiments, the set of predictor values comprises hexamer score; and motif accumulation.

In another aspect, the method also includes the steps of discounting, at 108, unreliable quality scores at the end of each read. The method 100 may also include identifying, at 110, reads where the second worst chastity in the first 25 base calls is below a pre-established threshold and marking the reads as poor quality data.

In another aspect, the discounting, at 108, may include using an algorithm to identify a threshold of reliability.

In another aspect, reliable base calls include q-values, or other values indicative of data quality or statistical significance, above the threshold and unreliable base calls comprise q-values, or other values indicative of data quality or statistical significance, below the threshold.

In another aspect, the algorithm comprises an End Anchored Maximal Scoring Segments (EAMSS) algorithm.

In another aspect, the algorithm uses a Hidden Markov Model that identifies shifts in the local distributions of quality scores.

In an embodiment, a system for evaluating the quality of a base call from a sequencing read is provided. The system includes a processor, a storage capacity, and a program for evaluating the quality of a base call from a sequencing read. The program includes instructions for (a) calculating a set of predictor values for the base call and (b) using the predictor values to look up a quality score in a quality table.

In another aspect, the sequencing read utilizes two-channel base calling.

In another aspect, the sequencing read utilizes one-channel base calling.

In another aspect, the quality table is generated using Phred scoring on a calibration data set, the calibration set being representative of run and sequence variability.

In another aspect, the predictor values are selected from the group consisting of: online overlap; purity; phasing; start5; hexamer score; motif accumulation; endiness; approximate homopolymer; intensity decay; penultimate chastity; and signal overlap with background (SOWB). Optionally, the set of predictor values comprises online overlap; purity; phasing; and start5. Optionally, the set of predictor values comprises hexamer score; and motif accumulation.

In another aspect, the program also includes instructions for (c) discounting unreliable quality scores at the end of each read and (d) identifying reads where the second worst chastity in the first 25 base calls is below a pre-established threshold and marking the reads as poor quality data.

In another aspect, step (c) may include using an algorithm to identify a threshold of reliability.

In another aspect, reliable base calls comprise q-values, or other values indicative of data quality or statistical significance, above the threshold and unreliable base calls comprise q-values, or other values indicative of data quality or statistical significance, below the threshold.

In another aspect, the algorithm comprises an End Anchored Maximal Scoring Segments (EAMSS) algorithm.

In another aspect, the algorithm uses a Hidden Markov Model that identifies shifts in the local distributions of quality scores.

Figure 7:
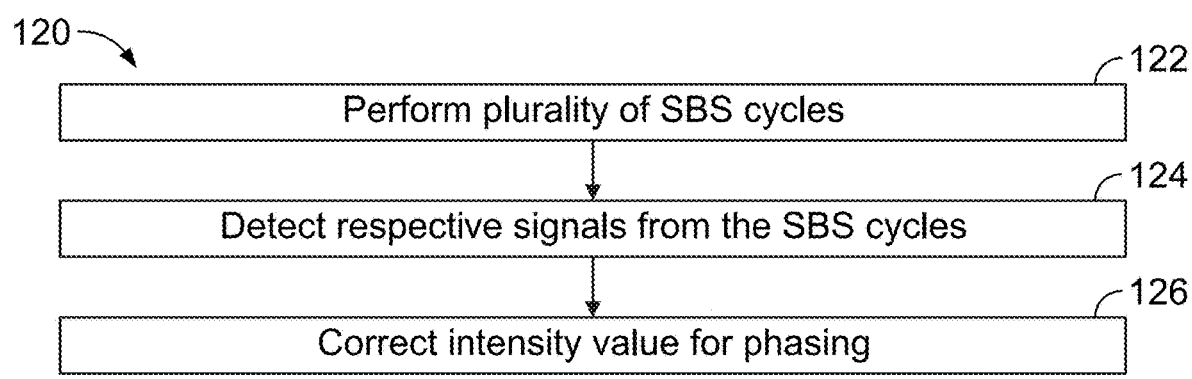
FIG. 7 is a flow chart illustrating a method in accordance with an embodiment.

FIG. 7 illustrates a method 120 in accordance with an embodiment. The method 120 may include, for example, a method of generating a phasing-corrected intensity value. The method includes (a) performing, at 122, a plurality of cycles of a sequencing by synthesis reaction such that, at each cycle, a signal is generated indicative of incorporation of the same nucleotide into a plurality of identical polynucleotides, whereby a portion of the signal is noise associated with a nucleotide incorporated during a previous cycle. The method also includes (b) detecting, at 124, the signal at each cycle. The signal has an intensity value. The method 120 also includes (c) correcting, at 126, the intensity value for phasing by applying a first order phasing correction to the intensity value, wherein a new first order phasing correction is calculated for each cycle.

In one aspect, the first order phasing correction comprises subtracting an intensity value from the immediately previous cycle from the intensity value of the current cycle.

In another aspect, the method includes subtracting an intensity value from the immediately subsequent cycle from the intensity value of the current cycle.

In another aspect the phasing correction comprises:

$$I_{(cycle)corrected} = I_{(cycle)\ N} - X * I_{(cycle)\ N-1} - Y * I_{(cycle)\ N+1}.$$

In another aspect, the values of X and/or Y are chosen to optimize a chastity determination. Optionally, the chastity determination comprises mean chastity.

In another aspect, the sequencing run utilizes two-channel base calling.

In another aspect, the sequencing run utilizes one-channel base calling.

In another aspect, the sequencing run utilizes four-channel base calling.

In an embodiment, a system for generating a phasing-corrected intensity value is provided. The system includes a processor, a storage capacity, and a program for generating a phasing-corrected intensity value. The program includes instructions for (a) performing a plurality of cycles of a sequencing by synthesis reaction such that, at each cycle, a signal is generated indicative of incorporation of the same nucleotide into a plurality of identical polynucleotides, whereby a portion of the signal is noise associated with a nucleotide incorporated during a previous cycle. The program includes instructions for (b) detecting the signal at each cycle, wherein the signal has an intensity value, and (c) correcting the intensity value for phasing by applying a first order phasing correction to the intensity value. A new first order phasing correction is calculated for each cycle.

In one aspect, the first order phasing correction comprises subtracting an intensity value from the immediately previous cycle from the intensity value of the current cycle.

In another aspect, the method includes subtracting an intensity value from the immediately subsequent cycle from the intensity value of the current cycle.

In another aspect, the phasing correction comprises:

$$I_{(cycle)corrected} = I_{(cycle)\,N} - X*I_{(cycle)\,N-1} - Y*I_{(cycle)\,N+1}.$$

In another aspect, the values of X and/or Y are chosen to optimize a chastity determination. Optionally, the chastity determination comprises mean chastity.

In another aspect, the sequencing run utilizes two-channel base calling.

In another aspect, the sequencing run utilizes one-channel base calling.

In another aspect, the sequencing run utilizes four-channel base calling.

Figure 8:
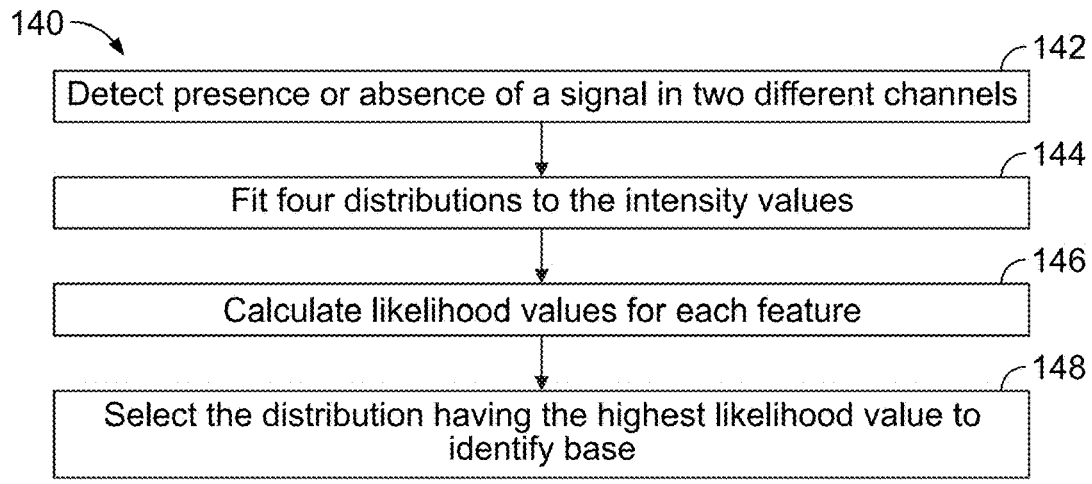
FIG. 8 is a flow chart illustrating a method in accordance with an embodiment.

FIG. 8 illustrates a method 140 in accordance with an embodiment. The method 140 may be, for example, a method of identifying a nucleotide base. The method 140 includes detecting, at 142, the presence or absence of a signal in two different channels for each of a plurality of features on an array at a particular time, thereby generating a first set of intensity values and a second set of intensity values for each of the features. The combination of intensity values in each of the two channels corresponds to one of four different nucleotide bases. The method also includes, at 144, fitting four Gaussian distributions to the intensity values. Each distribution has a centroid. The method also includes calculating, at 146, a likelihood value that indicates the likelihood of a particular feature belonging to each of the four distributions. The method also includes selecting, at 148, for each feature of said plurality of features the distribution having the highest likelihood value. This distribution corresponds to the identity of the nucleotide base present at the particular feature.

In one aspect, fitting includes using one or more algorithms from the group consisting of: a k-means clustering algorithm, a k-means-like clustering algorithm, an Expectation Maximization algorithm, and a histogram based method. In particular embodiments, fitting includes using an Expectation Maximization algorithm.

In another aspect, the method includes normalizing the intensity values.

In another aspect, a chastity value is calculated for each feature. The chastity value may be a function of the relative distance from a feature to the two nearest Gaussian centroids.

In another aspect, features having a chastity value below a threshold value are filtered out.

In an embodiment, a system for evaluating the quality of a base call from a sequencing read is provided. The system includes a processor, a storage capacity, and a program for identifying a nucleotide base. The program includes instructions for detecting the presence or absence of a signal in two different channels for each of a plurality of features on an array at a particular time, thereby generating a first set of intensity values and a second set of intensity values for each of the features. The combination of intensity values in each of the two channels corresponds to one of four different nucleotide bases. The program also includes instructions for fitting four Gaussian distributions to the intensity values. Each distribution has a centroid. The program also includes instructions for calculating a likelihood value that indicates the likelihood of a particular feature belonging to each of the four distributions and selecting for each feature of said plurality of features the distribution having the highest likelihood value. Said distribution corresponds to the identity of the nucleotide base present at said particular feature.

In one aspect, fitting includes using one or more algorithms from the group consisting of: a k-means clustering algorithm, a k-means-like clustering algorithm, an Expectation Maximization algorithm, and a histogram based method. In particular embodiments, fitting comprises using an Expectation Maximization algorithm.

In another aspect, the program includes instructions for normalizing the intensity values.

In another aspect, the program includes instructions for calculating a chastity value for each feature. The chastity value may be a function of the relative distance from a feature to the two nearest Gaussian centroids. Optionally, features having a chastity value below a threshold value are filtered out.

Figure 9:
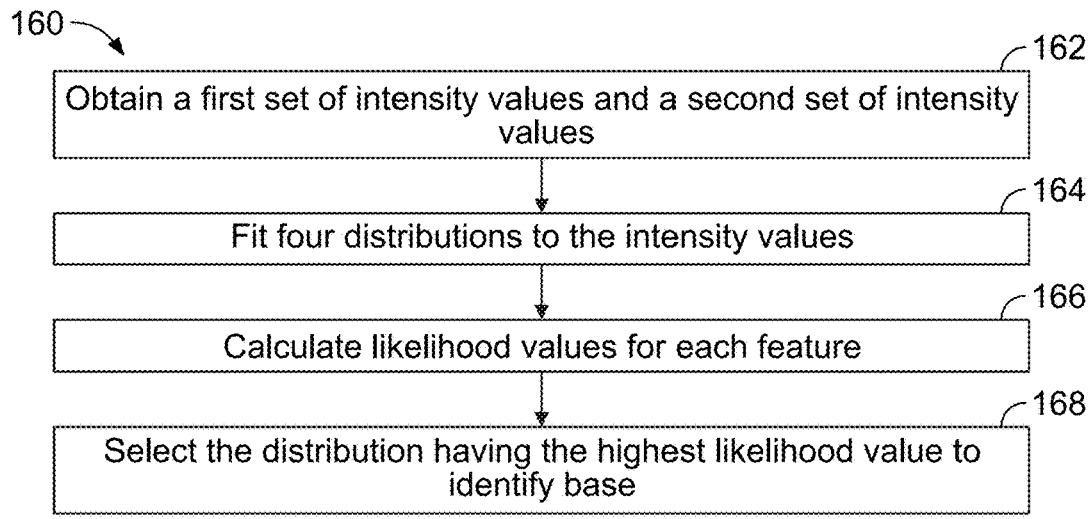
FIG. 9 is a flow chart illustrating a method in accordance with an embodiment.

FIG. 9 illustrates a method 160 in accordance with an embodiment. The method 160 may be, for example, a method of identifying a nucleotide base. The method 160 includes obtaining, at 162, a first set of intensity values and a second set of intensity values for each of a plurality of features on an array. The intensity value for each feature in one or both sets corresponds to the presence or absence of a particular nucleotide base out of four possible nucleotide bases at the feature. The method also includes fitting, at 164, four Gaussian distributions to the intensity values. Each distribution has a centroid. The method also includes calculating, at 166, four likelihood values for each feature, wherein each likelihood value indicates the likelihood of a particular feature belonging to one of the four distributions. The method also includes selecting, at 168, for each feature of said plurality of features the distribution having the highest of the four likelihood values. The distribution corresponds to the identity of the nucleotide base present at the particular feature.

In one aspect, fitting includes using one or more algorithms from the group consisting of: a k-means clustering algorithm, a k-means-like clustering algorithm, an Expectation Maximization algorithm, and a histogram based method. In particular embodiments, fitting includes using an Expectation Maximization algorithm.

In another aspect, the method also includes normalizing the intensity values.

In another aspect, a chastity value is calculated for each feature. The chastity value may be a function of the relative distance from a feature to the two nearest Gaussian centroids. Optionally, features having a chastity value below a threshold value are filtered out.

In an embodiment, a system for evaluating the quality of a base call from a sequencing read is provided. The system includes a processor, a storage capacity, and a program for identifying a nucleotide base. The program includes instructions for obtaining a first set of intensity values and a second set of intensity values for each a plurality of features on an array. The intensity value for each feature in one or both sets corresponds to the presence or absence of a particular nucleotide base out of four possible nucleotide bases at the feature. The program includes instructions for fitting four Gaussian distributions to the intensity values. Each distribution has a centroid. The program includes instructions for calculating four likelihood values for each feature, wherein each likelihood value indicates the likelihood of a particular feature belonging to one of the four distributions. The program includes instructions for selecting for each feature of said plurality of features the distribution having the highest of the four likelihood values, wherein the distribution corresponds to the identity of the nucleotide base present at the particular feature.

In one aspect, fitting includes using one or more algorithms from the group consisting of: a k-means clustering algorithm, a k-means-like clustering algorithm, an Expectation Maximization algorithm, and a histogram based method. In particular embodiments, fitting includes using an Expectation Maximization algorithm.

In another aspect, the program includes instructions normalizing the intensity values.

In another aspect, a chastity value is calculated for each feature. Optionally, the chastity value is a function of the relative distance from a feature to the two nearest Gaussian centroids. Optionally, features having a chastity value below a threshold value are filtered out.

Figure 10:
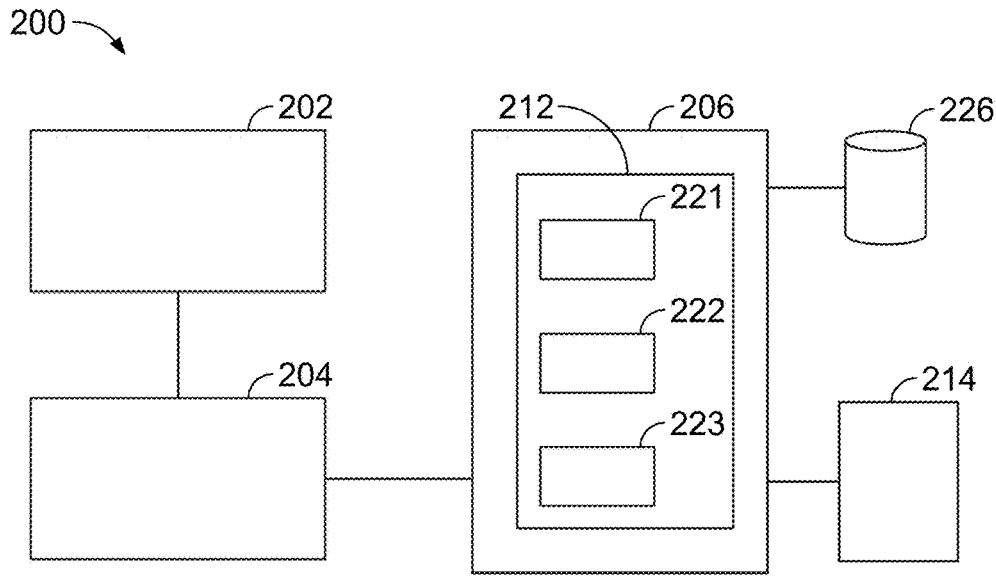
FIG. 10 is a block diagram of a system in accordance with an embodiment.

FIG. 10 illustrates a system 200 formed in accordance with an embodiment that may be used to carry out various methods set forth herein. For example, the system 200 may be used to carry out one or more of the methods 100 (FIG. 6), 120 (FIG. 7), 140 (FIG. 8), or 160 (FIG. 9). Various steps may be automated by the system 200, such as sequencing, whereas one or more steps may be performed manually or otherwise require user interaction. In particular embodiments, the user may provide a sample (e.g., blood, saliva, hair semen, etc.) and the system 200 may automatically prepare, sequence, and analyze the sample and provide a genetic profile of the source(s) of the sample. In some embodiments, the system 200 is an integrated standalone system that is located at one site. In other embodiments, one or more components of the system are located remotely with respect to each other.

As shown, the system 200 includes a sample generator 202, a sequencer 204, and a sample analyzer 206. The sample generator 202 may prepare the sample for a designated sequencing protocol. For example, the sample generator may prepare the sample for SBS. The sequencer 204 may conduct the sequencing to generate the sequencing data. As described above, the sequencing data may include a plurality of sequencing reads that include numerous base calls.

The sample analyzer 206 may receive the sequencing data from the sequencer 204. FIG. 10 includes a block diagram of a sample analyzer 206 formed in accordance with one embodiment. The sample analyzer 206 may be used to, for example, analyze sequencing reads to provide a base calls. The sample analyzer 206 includes a system controller 212 and a user interface 214. The system controller 212 is communicatively coupled to the user interface 214 and may also be communicatively coupled to the sequencer 204 and/or the sample generator 202.

In an exemplary embodiment, the system controller 212 includes one or more processors/modules configured to process and, optionally, analyze data in accordance with one or more methods set forth herein. For instance, the system controller 212 may include one or more modules configured to execute a set of instructions that are stored in one or more storage elements (e.g., instructions stored on a tangible and/or non-transitory computer readable storage medium, excluding signals) to process the sequencing data. The set of instructions may include various commands that instruct the system controller 212 as a processing machine to perform specific operations such as the workflows, processes, and methods described herein. By way of example, the sample analyzer 206 may be or include a desktop computer, laptop, notebook, tablet computer, or smart phone. The user interface 214 may include hardware, firmware, software, or a combination thereof that enables an individual (e.g., a user) to directly or indirectly control operation of the system controller 212 and the various components thereof.

In the illustrated embodiment, the system controller 212 includes a plurality of modules or sub-modules that control operation of the system controller 212. For example, the system controller 212 may include modules 221-223 and a storage system (or storage capacity) 226 that communicates with at least some of the modules 221-223. The modules 221-223 may be programs in some embodiments. The modules include a phase-correcting module 221, a quality evaluation module 222, and a base identifying module 223. The system 200 may include other modules or sub-modules of the modules that are configured to perform the operations described herein. The phase-correcting module 221 is configured to generate a phasing-corrected intensity value as set forth herein. The quality evaluation module 222 is configured to evaluate the quality of a base call from a sequencing read as set forth herein. The base identifying module 223 is configured to identify a nucleotide base as set forth herein.

As used herein, the terms "module", "system," or "system controller" may include a hardware and/or software system and circuitry that operates to perform one or more functions. For example, a module, system, or system controller may include a computer processor, controller, or other logic-based device that performs operations based on instructions stored on a tangible and non-transitory computer readable storage medium, such as a computer memory. Alternatively, a module, system, or system controller may include a hard-wired device that performs operations based on hard-wired logic and circuitry. The module, system, or system controller shown in the attached figures may represent the hardware and circuitry that operates based on software or hardwired instructions, the software that directs hardware to perform the operations, or a combination thereof. The module, system, or system controller can include or represent hardware circuits or circuitry that include and/or are connected with one or more processors, such as one or computer microprocessors.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

In some embodiments, a processing unit, processor, module, or computing system that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

Moreover, the operations of the methods described herein can be sufficiently complex such that the operations cannot be mentally performed by an average human being or a person of ordinary skill in the art within a commercially reasonable time period. For example, the methods may rely on relatively complex computations such that such a person cannot complete the methods within a commercially reasonable time.

What is claimed is:

1. A method comprising:
   (a) performing a plurality of cycles of a sequencing by synthesis reaction such that, at each cycle, a signal is generated that is indicative of incorporation of a same nucleotide into a plurality of identical polynucleotides, whereby a portion of the signal is noise associated with phasing or pre-phasing;

(b) detecting the signal at each cycle in at least one channel, wherein the signal at each cycle includes an intensity value for each channel; and (c) preforming cycle-by-cycle phasing corrections by applying a new first order phasing correction at each cycle to the intensity value for each channel;

wherein the new first order phasing correction is calculated for each channel of each cycle, wherein the new first order phasing correction includes subtracting an intensity value of an immediately previous cycle from an intensity value of a current cycle and also includes subtracting an intensity value of an immediately subsequent cycle from the intensity value of the current cycle; and wherein the same nucleotide incorporated into the plurality of identical polynucleotides is identified for each cycle.

2. The method of claim 1, wherein the at least one channel includes first and second channels and the same nucleotide is identified at each cycle through two-channel base calling that is performed by extracting image data from only two channels.

3. The method of claim 1, wherein the new first order phasing correction includes phasing and pre-phasing weights and the method further comprises selecting the phasing and pre-phasing weights from a plurality of possible phasing and pre-phasing weights.

4. The method of claim 3, wherein the phasing and pre-phasing weights are selected using a pattern search over the possible phasing and pre-phasing weights.

5. The method of claim 1, wherein detecting the singal at each cycle in the at least one channel includes detecting the singal in only one channel.

6. The method of claim 1, wherein the signal is detected from a first channel, a second channel, a third channel, and a fourth channel.

7. The method of claim 1, wherein optimal phasing and pre-phasing weights of the new first order phasing correction are chosen for each cycle by iterating over different phasing corrections calculated with different phasing and pre-phasing weights.

8. The method of claim 1, wherein phasing and pre-phasing weights of the new first order phasing correction are chosen to optimize a chastity determination for the current cycle.

9. The method of claim 8, wherein the chastity determination is a mean chastity for the current cycle.

10. A system comprising:
a processor;
a storage capacity; and
a program comprising instructions for:
(a) performing a plurality of cycles of a sequencing by synthesis reaction such that, at each cycle, a signal is generated that is indicative of incorporation of a same nucleotide into a plurality of identical polynucleotides, whereby a portion of the signal is noise associated with phasing or pre-phasing;
(b) detecting the signal at each cycle in at least one channel, wherein the signal at each cycle includes an intensity value for each channel; and
(c) performing cycle-by-cycle phasing corrections by applying a new first order phasing correction at each cycle to the intensity value for each channel;

wherein the new first order phasing correction is calculated for each channel at each cycle, wherein the new first order phasing correction includes subtracting an intensity value of an immediately previous cycle from an intensity value of a current cycle and also includes subtracting an intensity value of an immediately subsequent cycle from the intensity value of the current cycle; and wherein the same nucleotide incorporated into the plurality of identical polynucleotides is identified for each cycle.

11. The system of claim 10, wherein the new first order phasing correction includes phasing and pre-phasing weights and the program includes instructions for selecting the phasing and pre-phasing weights from a plurality of possible phasing and pre-phasing weights.

12. The system of claim 10, wherein the signal is detected from only one channel.

13. The system of claim 10, wherein the signal is detected from a first channel, a second channel, a third channel, and a fourth channel.

14. The system of claim 10, wherein the program includes instructions for choosing optimal phasing and pre-phasing weights of the new first order phasing correction for each cycle by iterating over different phasing corrections calculated with different phasing and pre-phasing weights.

15. The system of claim 10, wherein the program includes instructions for choosing phasing and pre-phasing weights of the new first order phasing correction to optimize a chastity determination for the current cycle.

16. The system of claim 15, wherein the chastity determination is a mean chastity for the current cycle.

17. A method comprising:
(a) performing a plurality of cycles of a sequencing by synthesis reaction such that, at each cycle, a signal is generated that is indicative of incorporation of a same nucleotide into a plurality of identical polynucleotides, whereby a portion of the signal is noise associated with phasing or pre-phasing;
(b) detecting the signal at each cycle, wherein detecting the signal at each cycle includes detecting an intensity value in a first channel and detecting an intensity value in a second channel; and
(c) performing cycle-by-cycle phasing corrections by applying a new first order phasing correction to the intensity value in each of the first and second channels at each cycle;

wherein the new first order phasing correction is calculated for each of the first and second channels at each cycle, wherein the new first order phasing correction includes subtracting an intensity value of an immediately previous cycle from an intensity value of a current cycle and also includes subtracting an intensity value of an immediately subsequent cycle from the intensity value of a current cycle;

wherein the same nucleotide incorporated into the plurality of identical polynucleotides is identified, for each cycle, based on a combination of the intensity values in the first and second channels.

18. The method of claim 17, wherein a first nucleotide is detected in the first channel, a second nucleotide is detected in the second channel, a third nucleotide is detected in both the first and the second channels, and a fourth nucleotide is not detected or is minimally detected by the first and second channels.

19. The method of claim 17, wherein the same nucleotide is one of four nucleotides and is identified through two-channel base calling at each cycle that includes fitting four Gaussian distributions to a data set of two-channel intensity data such that one Gaussian distribution is applied for each of the four nucleotides represented in the data set.

20. The method of claim 19, wherein the Gaussian distributions are fit to the data set using a clustering algorithm.

21. The method of claim 20, wherein the plurality of identical polynucleotides forms a cluster that generates the signal and wherein performing the plurality of cycles inclues generating respective signals from multiple clusters, each of the clusters having a different plurality of identical nucleotides, each of the clusters having a pair of X, Y intensity values, X and Y referring to the first and second channels, respectively, wherein for each pair of X, Y intensity values a likelihood value is generated which represents a likelihood that a certain pair of X, Y intensity values belongs to one of the four Gaussian distributions.

22. The method of claim 21, wherein each pair of X, Y intensity values has four likelihood values, one for each of the four nucleotides, a maximum of the four likelihood values indicating an identity of the same nucleotide.

23. The method of claim 20, further comprising filtering low chastity data points by determining a chastity of each of the data points as a function of relative di stances to Gaussian centroids.

* * * * *

UNITED STATES PATENT AND TRADEMARK OFFICE
CERTIFICATE OF CORRECTION

PATENT NO. : 10,689,696 B2
APPLICATION NO. : 15/153953
DATED : June 23, 2020
INVENTOR(S) : Paul Belitz et al.

Page 1 of 1

It is certified that error appears in the above-identified patent and that said Letters Patent is hereby corrected as shown below:

In the Claims

Claim 1, Column 45, Line 7, delete "preforming" and insert -- performing --, therefor.

Claim 5, Column 45, Line 35, delete "singal" and insert -- signal --, therefor.

Claim 5, Column 45, Line 37, delete "singal" and insert -- signal --, therefor.

Claim 17, Column 46, Line 55, delete "a" and insert -- the --, therefor.

Claim 17, Column 46, Line 59, delete "channels." and insert -- channels after applying the new first order phasing correction for each of the first and second channels. --, therefor.

Claim 21, Column 47, Line 9, delete "inclues" and insert -- includes --, therefor.

Claim 23, Column 47, Line 24, delete "di stances" and insert -- distances --, therefor.

Signed and Sealed this
Eighteenth Day of August, 2020

Andrei Iancu
*Director of the United States Patent and Trademark Office*